United States Patent [19]

Ruell

[11] 4,385,831
[45] May 31, 1983

[54] DEVICE FOR INVESTIGATION OF A FINGER RELIEF

[75] Inventor: Hartwig Ruell, Fürstenfeldbruck, Fed. Rep. of Germany

[73] Assignee: Siemens Corporation, Iselin, N.J.

[21] Appl. No.: 189,176

[22] Filed: Sep. 22, 1980

[51] Int. Cl.³ .......................... G06K 9/00; G06K 9/28
[52] U.S. Cl. ..................................... 356/71; 350/3.71; 382/4
[58] Field of Search .................. 356/71, 394; 250/566; 340/146.3 E; 350/3.71

[56] References Cited

U.S. PATENT DOCUMENTS

| | | | |
|---|---|---|---|
| 3,201,961 | 8/1965 | Williams et al. | 356/71 |
| 3,516,059 | 6/1970 | Hindman et al. | 340/146.3 E |
| 3,961,838 | 6/1976 | Zanoni . | |
| 4,053,228 | 10/1977 | Schiller | 356/71 |
| 4,120,585 | 10/1978 | DePalma et al. | 356/71 |
| 4,227,805 | 10/1980 | Schiller . | |

FOREIGN PATENT DOCUMENTS 950587  7/1974  Canada ............................... 356/394

OTHER PUBLICATIONS

"Remote Measurement of Distance and Thickness Using a Deflected Laser Beam", Bodlaj et al., Applied Optics, vol. 15 #6, Jun. 76, pp. 1432–1436.

*Primary Examiner*—Vincent P. McGraw
*Attorney, Agent, or Firm*—Karl F. Milde, Jr.

[57] ABSTRACT

The fingerprint sensor device derives an electric output signal in accordance with the topographic relief of a finger under investigation. The sensor incorporates a radiation source, a fingerbed, a first radiation transmitting device, a scanning device, a second radiation transmitting device, and a measuring device responsive to the radiation. The fingerbed has an opening for passing a beam of radiation (light or ultrasound, for instance) from the source therethrough. The scanning device scans this beam of radiation across the finger. Thus, the finger relief is directly scanned by a beam of small impingement spot. The back scattered radiation is directed to the measuring device. Here, the intensity distribution is determined.

7 Claims, 5 Drawing Figures

U.S. Patent May 31, 1983 4,385,831
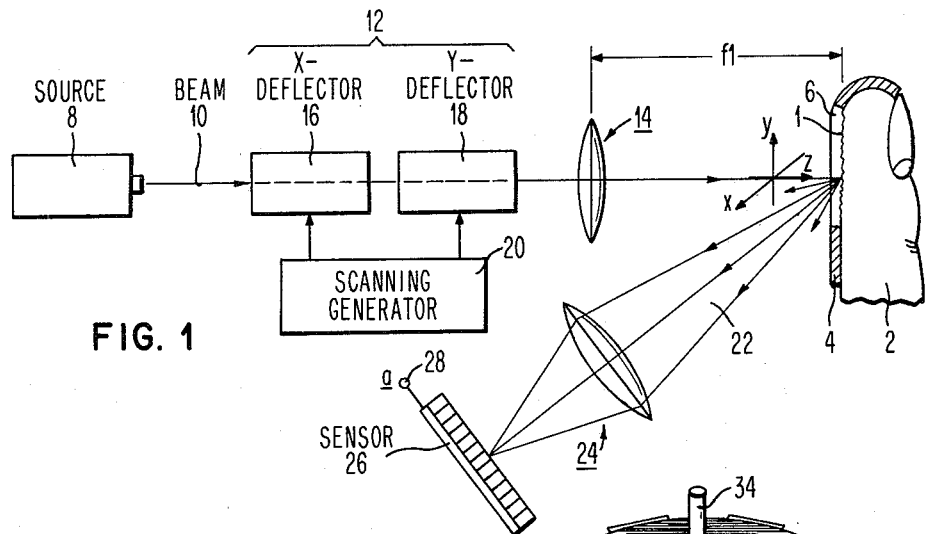
FIG. 1
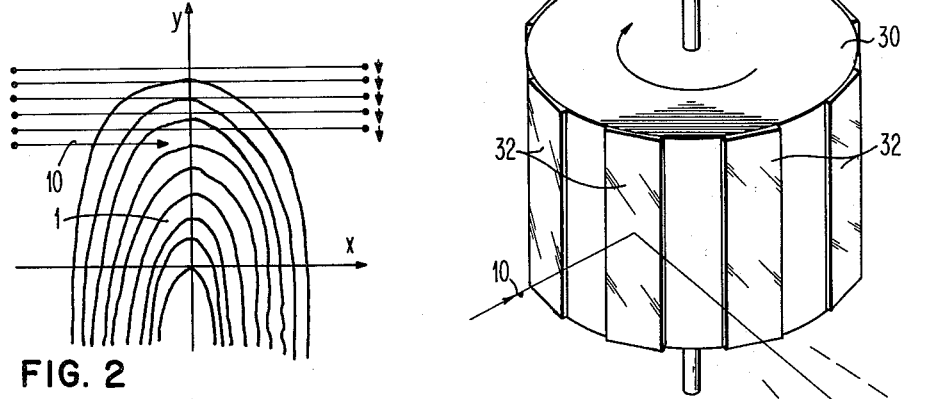
FIG. 2
FIG. 3
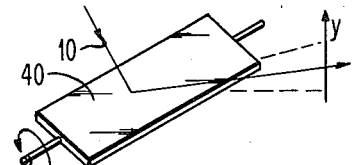
FIG. 4
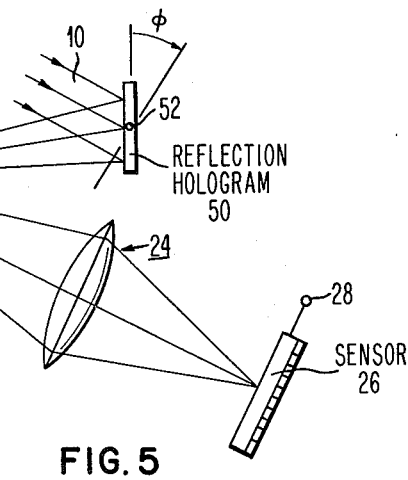
FIG. 5

DEVICE FOR INVESTIGATION OF A FINGER RELIEF

BACKGROUND OF THE INVENTION

1. Field of the Invention

This invention relates in general to a device for identifying an individual by identification of his/her fingerprint. In particular, this invention relates to a device for investigating a finger relief, and more particularly, to a sensor for transforming the information contained in a person's fingerprint into an output signal. Still more particularly, this invention relates to a sensor using scanning means for reading a fingerprint.

2. Desription of the Prior Art

Fingerprint identification systems which identify the print of a finger pressed on a contact surface are well-known in the art.

U.S. Pat. No. 4,053,228, for instance, discloses a finger identification apparatus which contains a transparent glass plate serving as a contact surface or fingerprint reader. A fingerprint is formed by pressing the finger under investigation against the back surface of the glass plate and holding it in a predetermined position thereon. The fingerprint is interrogated by a light beam directed through the front surface of the glass plate. The interrogating beam is partially reflected at the back surface to provide a signal beam which carries the fingerprint information. The reflected signal beam is then correlated against a hologram of the same fingerprint in order to provide the identification of the individual.

In U.S. Pat. No. 4,120,585, another fingerprint identification system is disclosed. This system contains a pliable optical prism as a fingerprint sensor. The base of the prism is physically contacted by the finger of the person under investigation. The pliable prism deforms broadly under the applied pressure. It partially reflects a sensing light beam to a photo-sensitive device which will be activated. The photo-sensitive device, in turn, activates further optical components of the fingerprint identification system. A fingerprint reader is examined for the ridge-valley pattern of the fingerprint of a person to be identified.

The prior fingerprint identification systems require highly sophisticated technology. Yet, a fingerprint identification system should easily and inexpensively be assembled, and simultaneously it should afford a high image quality of the fingerprints. Particularly, the fingerprint image should be free from distortions.

SUMMARY OF THE INVENTION

Objects

It is an object of this invention to provide a fingerprint sensor for transforming the fingerprint information of a finger into an output signal, especially into an electric output signal.

It is another object of this invention to provide a fingerprint sensor the electric output signal of which represents the information contained in the fingerprint and can be read into a computer or into other electronic apparatus for further processing.

It is still another object of this invention to provide a fingerprint sensor which is easy to assemble, which requires low cost, which provides high sensitivity and resolution, and which affords a high reliability.

It is still another object of this invention to provide a fingerprint sensor for transforming the fingerprint information of a finger using scanning techniques.

Summary

According to this invention, a device for investigating the pattern of a finger incorporates a source for emitting a beam of radiation. This beam can either be a beam of electro-magnetic waves or a beam of ultrasonic waves. Preferably, light may be used, either infrared light, visible light, or ultraviolet light.

The investigation device also incorporates a finger supporting device or fingerbed. The finger is introduced onto this fingerbed when an investigation is made. The fingerbed serves to keep the finger skin free from distortions when the pattern of the finger is sensed. In order that the beam of radiation from said source may have access to the skin of the finger, the fingerbed defines an opening or hole. When the finger rests in the fingerbed for investigation, the beam of radiation is directed through this opening directly onto the skin. In other words, the opening or hole leaves free an area of the finger skin for direct irradiation and investigation.

The investigation device further incorporates a first beam directing device for passing the beam of radiation to the area under investigation, and a scanning device. The beam directing device and the scanning device may be combined in a single apparatus. Under the influence of the beam directing device, the beam of radiation forms a spot of impingement on the skin area under investigation. In order to obtain sufficient resolution, the extension of this spot must be smaller than the distance between any two adjacent ridges or valleys of the skin area. Preferably, a focussing device may be used to obtain a small spot on the finger skin. The scanning device scans the spot of impingement across the skin area. Scanning is performed line by line. It is possible to start from a first side and to proceed to the other or second side, then to switch over to the next line and start from the second side proceeding to the first side. The impinging radiation will be scattered or reflected in accordance with the ridge-valley pattern of the skin. As the impingement spot passes along the scanning lines, the intensity of the back scattered or reflected radiation contains the information about the topology of the finger skin.

This finger information is transformed into an electric output signal by electrical components of the finger pattern detecting device. The investigation device further incorporates a measuring device which is responsive to the reflected or back scattered radiation. It also contains a second beam directing device for transmitting the back scattered beam of radiation to the measuring device. In an embodiment where light is used as the sensing radiation, the measuring device may be a photodetector such as a CCD array or a video camera, and the second beam deflecting device may be an imaging lens or an imaging lens system. The measuring device preferably measures the local intensity distribution of the back scattered radiation. The result of the measurement will be in accordance with the ridge-valley pattern of the finger area under investigation. An output which is associated with the measuring device will deliver a corresponding output signal. This signal, which is preferably an electric signal, may be further processed, either in a computer or in other electronic processing means. The output signal may also be displayed on a CRT screen.

According to this invention, the skin of the finger is scanned directly, that is without any additional interface material or device. As discussed above, scanning is performed with a suitably chosen radiation beam. The radiation scattered back by the skin of the finger is modulated in accordance with the topology of the finger skin. The back scattered radiation thus contains all information about the pattern on the finger tip. The scattered radiation beam is transformed into an electric output signal which can easily be evaluated by processing means.

The foregoing and other objects, features and advantages of the invention will be apparent from the following more particular description of preferred embodiments of the invention, as illustrated in the accompanying drawings.

BRIEF DESCRIPTION OF THE DRAWINGS

In the drawings

FIG. 1 is a first schematic diagram of a finger investigation device incorporating direct scanning of a finger, in accordance with this invention;

FIG. 2 is a skin pattern of a finger which is scanned by a beam of radiation in accordance with this invention;

FIG. 3 is a perspective view of an optical deflector containing rotating polygon mirrors;

FIG. 4 is a perspective view of an optical deflector which is rotatable about an axis in a step by step operation; and FIG. 5 is a second schematic diagram of a finger investigation device incorporating direct scanning of a finger, in accordance with this invention.

DETAILED DESCRIPTION OF THE PREFERRED EMBODIMENTS

According to FIG. 1, a device for investigating the skin pattern 1 on the tip of a finger 2 is illustrated. The investigation device contains a suitably designed support or fingerbed 4, in which the finger can rest. The fingerbed 4 contains an opening or hole 6 which leaves free the area of the finger skin which shall be investigated. In other words, there is no material provided against which the finger area under investigation is pressed during a sensing process. Therefore, an examination beam (which will be described in more detail below) may freely pass through the hole 6 having direct access to the finger surface 1. The fingerbed 4 is used to keep the finger 2 in a fixed position during investigation. Since there is no covering material, the finger surface, that is the pattern of valley and crests of the skin, is directly exposed to the examining beam of radiation.

The investigation device also incorporates a source 8 for emitting a beam of radiation 10. The beam 10 is passed through a scanning device 12 and a beam directing device 14 to the skin pattern 1. The beam directing device 14 causes the beam 10 to form a small spot of impingement on the skin area under investigation. This spot is smaller in diameter than the distance between two adjacent ridges or valleys on the skin.

The scanning device 12 contains an x-deflector 16 for deflecting the beam 10 in an x-direction and a y-deflector 18 for deflecting the beam 10 in a y-direction. The deflectors 16 and 18 are arranged one behind the other. The directions x and y are perpendicular with respect to each other, and perpendicular with respect to the travelling direction z of the beam 10. The x-deflector 16 and the y-deflector 18 are both controlled by a scanning generator 20. The scanning generator 20 synchronizes the x-deflection with respect to the y-deflection.

The scanning device 12 scans the impingement spot across the area 11 under investigation. As a result, the finger area will scatter back a beam of radiation 22 which is modulated in accordance with the structure or pattern on the area under investigation. The scattered wave 22 is directed via a beam directing device 24 to a sensing or measuring device 26 which is responsive to the radiation of the source 8. The measuring device 26 measures the distribution of the back scattered radiation which is in accordance with the ridge-valley pattern of the area 1 under investigation. Associated with the measuring device 26 is an output 28 for deriving an electric output signal a.

In FIG. 2 is illustrated in which way the spot of impingement may be scanned across the skin pattern 1. As can be seen, the beam 10 is scanned line by line in x-direction which movement is performed by the x-deflector 16. A motion from line to line in y-direction is carried out by the y-deflector 18. In each line, the beam 10 starts on the left side and proceeds to the right side.

Ultrasonic radiation may be used for scanning the finger 2. In an embodiment using ultrasound techniques, the devices 8, 16, 18, 14, 24 and 26 must be ultrasound components. An ultrasound source 8 and deflectors 16 and 18 for scanning the finger 2 with an ultrasound beam 10 as well as other ultrasound components 14, 24 and 26 are commercially available.

Preferably, however, the scanning radiation beam 10 may be an electro-magnetic radiation beam. Infrared light, visible light, or ultraviolet light may be used. The electro-magnetic radiation may especially be a monochromatic radiation which is spatially coherent.

In a preferred embodiment, which will subsequently be discussed, the source 8 may be a laser which emits a monochromatic and parallel light beam 10. The light beam 10 is focussed onto the skin of the finger 2 by a beam directing device 14 which is shown to be a focussing lens. Also, a focussing system containing an assembly of lenses may be used. The focussing lens is positioned at a distance $f_1$ in front of the finger 2. This distance $f_1$ corresponds to the focal length of the lens or lens system. Therefore, the laser beam 10 is focussed on the pattern 1, and a very small spot of impingement can be obtained.

In the preferred optical implementation of the sensing device, the back scattered light 22 is received by a suitably designed imaging device which is used as the second beam directing device 24. The imaging device may contain a lens, a hologram, a Fresnel zone mirror, which may be curved, and similar devices. The light imaging device 24 creates an image of the finger structure 1 on the measuring device 26.

The measuring device 26 may contain a photodetector which has a light sensitive area for measuring the distribution of light impinging thereon. The light sensitive area may be a single sensor area or may be comprised of an array of sensor elements. Particularly, a CCD array or a video camera can be used. The scattered light which is imaged onto the light sensitive area is transformed into the electric output signal a in accordance with the intensity distribution. The measuring device 26 may feed the information contained in the output signal a into further processing electronics (not shown) for further evaluation.

As indicated previously, the source 8 may be a laser. It may be a HE-Cd laser, a He-Ne laser, or a semiconductor laser.

Any of the deflectors 16 may be a galvanometer mirror, an acousto-optical beam deflector, an electro-optical beam deflector, a vibrating fork with mirrors attached, a spinning mirror polygon, an opto-mechanical beam deflector such as a piezoceramic beam deflector (Applied Optics, Vol. 15, pages 1432-36, June 1976, FIG. 5), etc. Beam deflectors of various kinds are commercially available.

The first beam directing device 14 may be a focussing lens. For instance, it may be a simple glass lens, which is positioned at the focal length distance from the skin pattern 1. The second beam directing device 24 may be an imaging lens. For instance, it may be a simple glass lens which is capable of imaging the fingerprint pattern 1 without any distortion onto the light sensitive area of the measuring device 26.

As previously mentioned the source 8 may be a ultraviolet (UV) source. If illuminated by a UV source 8, the oil and moisture produced by the human skin on the finger 2 will emit fluorescent radiation which can be used to image the distribution or structure of the oil or moisture, respectively, onto the light sensitive area of the measuring device 26.

In FIG. 3, an optical deflector for scanning the finger 2 is illustrated. The light deflector contains a rotating cylinder 30 which is provided with mirrors 32 on its circumference. When the cylinder 30 rotates about its axis 34, the impinging light beam 10 is repeatedly deflected in x-direction by the mirrors 32.

As illustrated in FIG. 4, the deflector may be a mirror 40 which may be rotated in increments about a longitudinal axis 42. The impinging light beam 10 will be deflected in y-direction in a step by step operation.

In FIG. 5 another embodiment of an optical device for investigating the pattern 1 of a finger 2 is illustrated. In this embodiment, the light beam 10 which preferably may be emitted by a laser, may be focussed and simultaneously deflected by the same element. This element is a reflection hologram 50. The orientation $\rho$ in space may be changed according to a predetermined skin pattern. For this purpose, the reflecting hologram 50 is provided with a rotating axis 52. It will be noted that the light beam 10 is focussed onto the finger pattern 1 in an angle which is not equal to the reflection angle. By using a reflection hologram 50, an imaging lens 14 (see FIG. 1) can be avoided. The scattered wave 22 is evaluated in the same way as in FIG. 1.

There has thus been shown and described a novel fingerprint sensor which fulfills all the objects and advantages sought therefor. Changes, modifications, variations and other uses and applications of the subject invention will, however, become apparent to those skilled in the art after considering this specification and the accompanying drawings which disclose preferred embodiments thereof. All such changes, modifications, variations and other uses and applications which do not depart from the spirit and scope of the invention are deemed to be covered by the invention which is limited only by the claims which follow.

What is claimed:

1. A device for investigating the pattern of a finger, comprising in combination:
   (a) a source for emitting a beam of radiation;
   (b) a fingerbed for supporting said finger, said fingerbed defining an opening which leaves free an area of the skin of said finger for investigation, when said finger rests in said fingerbed;
   (c) means for passing said beam of radiation to said area under investigation, said beam thereby forming a spot of impingement on said area which has an extension that is smaller than the distance between two adjacent ridges on said skin under investigation;
   (d) means for raster scanning said impingement spot in two dimensions over said area under investigation, said finger skin area thereby scattering back a beam of radiation which is modulated in accordance with said pattern on said area, said scanning means comprising a reflection hologram which is tiltable about an axis;
   (e) measuring means responsive to said radiation;
   (f) lens means for collecting and transmitting said back-scattered beam of radiation to said measuring means, said measuring means thereby measuring the distribution of the back-scattered radiation in accordance with the ridge-valley pattern of said area under investigation; and
   (g) output means associated with said measuring means for producing an output signal representing the intensity of back-scattered radiation.

2. The device according to claim 1, wherein said radiation source is adapted to emit a beam of electromagnetic waves.

3. The device according to claim 2, wherein said radiation source is adapted to emit a light beam.

4. The device according to claim 3, wherein said light source is a laser.

5. The device according to claim 3, wherein said means for passing said beam of radiation to said finger contains a first lens for focussing said beam on said finger area.

6. The device according to claim 3, wherein said means for transmitting said reflected beam of radiation contains a second lens for casting an image of said finger area onto said measuring means.

7. The device according to claim 3, wherein said measuring means comprises a photodetector having a light sensitive area for measuring the distribution of light impinging on said area.

* * * * *